United States Patent [19]

Watanabe et al.

[11] 4,235,898

[45] Nov. 25, 1980

[54] LIQUID SHAMPOO COMPOSITION

[75] Inventors: Hiroshi Watanabe, Funabashi; Tsuruo Mikata, Kashiwa, both of Japan

[73] Assignee: Kao Soap Co., Ltd., Tokyo, Japan

[21] Appl. No.: 12,066

[22] Filed: Feb. 14, 1979

[30] Foreign Application Priority Data

Mar. 6, 1978 [JP] Japan ................................. 53-25147

[51] Int. Cl.$^3$ ............................................. A01N 55/02
[52] U.S. Cl. ................................... 424/245; 252/153; 252/154; 252/544; 252/545; 252/DIG. 2; 252/DIG. 13; 424/70
[58] Field of Search ............... 252/153, 154, 544, 545, 252/DIG. 13, DIG. 2; 424/70, 245

[56] References Cited

U.S. PATENT DOCUMENTS

| | | | |
|---|---|---|---|
| 3,179,595 | 4/1968 | Olsen, Jr. .......................... | 252/153 X |
| 3,332,878 | 7/1967 | Coward et al. ...................... | 252/153 |
| 3,755,206 | 8/1973 | Verdier ............................ | 252/153 X |

OTHER PUBLICATIONS

McCutcheons "Detergents & Emulsifiers, 1969, p. 62.

*Primary Examiner*—Mayer Weinblatt
*Attorney, Agent, or Firm*—Blanchard, Flynn, Thiel, Boutell & Tanis

[57] ABSTRACT

A liquid shampoo composition which possesses an excellent foaming power and in which a water-insoluble finely divided powder can be dispersed in a stable condition, in which a stabilizer selected from the group consisting of lower alcohols, glycols and alkanolamines is incorporated in a liquid shampoo composition containing an ammonium salt or an organic amine salt of an anionic surfactant, an ammonium salt or an organic amine salt of water-soluble polyacrylic acid, as principal ingredients, and also containing a fatty acid alkanolamide.

4 Claims, No Drawings

LIQUID SHAMPOO COMPOSITION

The present invention relates to a shampoo composition in which a water-insoluble finely divided powder can be dispersed in a stable condition.

A stable dispersion of a water-insoluble finely divided powder in a liquid shampoo composition has been employed frequently for the purpose of obtaining a pearlescent appearance or for increasing the commercial value of the shampoo by incorporating therein a hair- or scalp-treating medicament, a germicide or a suspending agent. In order to stably disperse a water-insoluble, finely divided powder in a liquid shampoo composition, the following two critical conditions must be satisfied:

(1) The dispersed fine particles must not coagulate, and (2) The dispersion has a high yield value.

As compositions capable of satisfying those conditions, there are considered compositions having a very high viscosity and thixotropic compositions having a non-Newtonian flow property. However, the former have only a poor fluidity and a liquid shampoo which is easy to use cannot be obtained from them. As for the latter, there has been known a technique disclosed in Japanese Patent Publication No. 49117/1974 wherein there is used the combination of an anionic surfactant comprising an ammonium salt or an amine salt substituted with an organic group and a water-soluble polyacrylic acid. The pH of such a composition is controlled to be in the range of 6 to 8 by means of an organic amine such as ammonia or an alkanolamine, thereby making it possible to stably disperse a water-insoluble finely divided powder therein.

The present invention relates to an improvement in the latter known technique. It is well known that the fundamental properties required of a shampoo are the foaming property and the deterging (cleaning) property. For achieving those properties, the use of an anionic surfactant alone is generally insufficient and it is necessary to incorporate a fatty acid alkanolamide or the like therein. It is no exaggeration to say that substantially all commercially available shampoos contain those two components as indispensable ingredients. However, it has been found that if a fatty acid alkanolamide is added to the composition disclosed in Japanese Patent Publication No. 49117/1974, the viscosity of the composition is reduced remarkably and the yield value becomes almost zero. As a result, if a water-insoluble finely divided powder is incorporated therein, said powder precipitates so that it is impossible to obtain a stable dispersion of the powder in the shampoo. Thus, according to the known techniques, it is impossible to incorporate a fatty acid alkanolamide in a liquid shampoo in which a water-insoluble finely divided powder is to be dispersed stably. In addition, it is difficult to prepare such a shampoo having an excellent foaming power and a high dispersion stability.

After intensive investigations for overcoming those defects, the inventors have accomplished the present invention.

The present invention provides a liquid shampoo composition which possesses an excellent foaming power and in which a water-insoluble finely divided powder can be dispersed in a stable condition. According to the invention, a stabilizer selected from the group consisting of lower alcohols, glycols and alkanolamines is incorporated in the liquid shampoo composition during the preparation thereof, wherein said liquid shampoo composition comprises a fatty acid alkanolamide, an ammonium salt or an organic amine salt of an anionic surfactant and an ammonium salt or an organic amine salt of water-soluble carboxy vinyl polymer as principal ingredients.

The amounts of the respective components of the composition according to the present invention comprise from 5 to 30 wt. %, preferably 10 to 20 wt. % of the anionic surfactant, from 0.1 to 1.0 wt. %, preferably 0.4 to 0.6 wt. %, of a salt of water-soluble carboxy vinyl polymer, from 1 to 10 wt. %, preferably 3 to 5 wt. %, of the fatty acid alkanolamide and from 1 to 20 wt. %, preferably 3 to 10 wt. % of the stabilizer.

As the anionic surfactants that are useful in the present invention, there can be mentioned, for example, ammonium salts and salts of amines substituted with organic groups, such as monoethanolamine salts, diethanolamine salts, triethanolamine salts and 2-amino-2-methylpropane-1,3-diol salts, of alkyl sulfates having 8-22 carbon atoms in the alkyl group, polyoxyethylene (1-10 moles) alkyl ether sulfates having 8 to 22 carbon in the alkyl group, polyoxyethylene (1-10 moles) alkylphenyl ether sulfates having 8 to 12 carbon atoms in the alkyl group, olefin sulfonates having 8-22 carbon atoms and alkylbenzene sulfonates having a straight or branched alkyl group of 9 to 18 carbon atoms, preferably 12 carbon atoms, on the average.

As the fatty acid alkanolamides that are useful in the present invention, there can be mentioned, for example, fatty acid monoethanolamides and diethanolamides having 10-14 carbon atoms in the fatty acid moiety.

As the lower alcohols that are useful in the present invention, alkanols having 1-3 carbon atoms are preferred. They are, for example, methyl alcohol, ethyl alcohol and isopropyl alcohol. As the glycols, those having 2-6 carbon atoms are preferred. They are, for example, ethylene glycol, diethylene glycol, propylene glycol, dipropylene glycol and hexylene glycol. As the alkanolamines, there can be mentioned, for example, monoethanolamine, diethanolamine and triethanolamine.

As the water-insoluble powders that are stably dispersible in the composition according to the present invention, there can be mentioned, for example, pigments such as calcium carbonate, barium carbonate, titanium white, Hansa Yellow, crushed rock and talc, abrasives, pearling agents or clouding agents such as mica and fish scales, and germicides and antiseptics such as zinc bis(2-pyridylthio)-1,1'-dioxide. The amount of the water-insoluble powder that is incorporated in the liquid shampoo composition is variable depending on the intended functional effect to be achieved thereby. In general, the amount of the powder is in the range of from 0.001 to 5.0 wt. %.

According to the invention, it is preferable to add to the shampoo composition an additive comprising ammonia or an organic amine and thereby to adjust a pH value of the composition within a range of from 6 to 8, so that the dispersion will be more stable.

We have not yet elucidated the reasons why the yield value and the viscosity are reduced and the dispersion stability is deteriorated seriously when the fatty acid alkanolamide is incorporated in the composition disclosed in Japanese Patent Publication No. 49117/1974 comprising the anionic surfactant (ammonium salt or organic amine salt) and ammonium salt or organic amine salt of water-soluble carboxy vinyl acid and having a high yield value in which the water-insoluble finely divided powder is dispersible stably. Lauric acid diethanolamide was incorporated as the fatty acid alkanolamide in the composition and the viscosity and percent of transmittance of the composition were measured. The test results are shown in Table 1. In this experiment, there were used compositions to which the water-insoluble finely divided powder was not added, because the percent of the transmittance thereof was to be measured.

TABLE 1

Change in viscosity and percent transmittance by incorporation of lauric acid diethanolamide

| Amount of lauric acid diethanolamide | Viscosity | Percent of transmittance (600 mμ) |
|---|---|---|
| 0 (wt. %) | 550 (cps) | 98 (%) |
| 0.5 | 320 | 67 |
| 1.0 | 210 | 41 |
| 2.0 | 150 | 36 |
| 3.0 | 110 | 20 |
| 5.0 | 190 | 15 |

Components of the composition other than lauric acid diethanolamide:

| Triethanolamine lauryl sulfate | 18 wt. % |
|---|---|
| Carboxy vinyl Polymer* | 0.6 |
| Triethanolamine | 2.4 |
| Water | Balance |

*Carboxy vinyl Polymer: Carbopole 941 (a product of Goodrich Co.)

It is apparent from Table 1 that as the amount of lauric acid diethanolamide added was increased, the viscosity of the composition was reduced sharply and the percent transmittance was also reduced. It is supposed that the phenomenon occurred because the carboxy vinyl polymer salt, that was dissolved in the aqueous solution of anionic surfactant, reacted with the lauric acid diethanolamide added thereto, thereby coagulating the carboxy vinyl polymer salt in the solution.

The above described lower alcohols, glycols and alkanolamines were added to a composition set forth below, which had a viscosity and a percent of transmittance which were reduced by the addition of lauric acid diethanolamide in the same manner as described above. Then the viscosities and percent of transmittance of those compositions were measured. The results shown in Table 2 were obtained.

TABLE 2

Recovery of viscosity and increase in percent of transmittance caused by the addition of a lower alcohol, glycol or alkanolamine

| Stabilizer | Amount | Viscosity | Percent of transmittance (600 mμ) |
|---|---|---|---|
| None | 0 | 110 cps | 20 % |
| Ethanol | 3 wt % | 390 | 85 |
| Methanol | 3 | 400 | 82 |
| Isopropanol | 3 | 350 | 79 |
| Propylene glycol | 8 | 410 | 80 |
| Glycerol | 10 | 320 | 71 |
| Ethylene glycol | 5 | 310 | 72 |
| Hexylene glycol | 5 | 420 | 83 |
| Triethanolamine | 7 | 360 | 76 |
| Diethanolamine | 10 | 420 | 83 |

Components of the composition other than the stabilizer:

| Triethanolamine laurylsulfate | 25.0 wt. % |
|---|---|
| Lauric acid diethanolamide | 4.0 |
| Carboxy vinyl Polymer (Carbopole 941) | 0.6 |
| Triethanolamine | 2.4 |
| Water | Balance |

It is apparent from Table 2 that if the lower alcohol, glycol or alkanolamine is added to a composition whose viscosity and percent of transmittance were reduced by the addition of lauric acid diethanolamide, the viscosity and percent of transmittance thereof are increased. It is supposed that this phenomenon occurs because the stabilizer prevents coagulation of the carboxy vinyl polymer salt, or if it does coagulate, it is dissolved again by the addition of the lower alcohol, gylcol or alkanolamine, whereby the viscosity and percent of transmittance of the composition are restored to high values.

The stabilities of compositions in which water-insoluble finely divided powder was dispersed were compared with one another. The results are shown in Table 3.

TABLE 3

| Amount of Lauric acid diethanolamide | Stabilizer and Amount | Viscosity of composition | Yield value** | Dispersion stability |
|---|---|---|---|---|
| None | None | 500 cps | 31 | O |
| 3 wt % | None | 120 | 0 | X |
| 3 | Propylene glycol 5 wt % | 320 | 23 | O |
| 3 | Ethanol 3 wt % | 410 | 26 | O |
| 3 | Triethanolamine 4 wt % | 280 | 21 | O |
| 3 | Hexylene glycol 5 wt % | 320 | 20 | O |
| 3 | Isopropyl alcohol 3 wt % | 380 | 23 | O |

**Yield value: Brookfield yield value

Components of the composition other than lauric acid diethanolamide and stabilizer:

| Triethanolamine laurylsulfate | 20 wt. % |
|---|---|
| Carboxy vinyl Polymer* | 0.5 |
| Titanium dioxide | 0.5 |
| Triethanolamine | 2.0 |
| Water | Balance |

*Carboxy vinyl Polymer: Carbopole 941 (a product of Goodrich Co.)

It is apparent from Table 3 that the dispersion stability of the finely divided powder in the composition is deteriorated seriously when only a fatty acid alkanolamide is incorporated therein, but the stability is restored by the further addition of the stabilizer of the present invention.

The following examples further illustrate the present invention.

EXAMPLE 1

A shampoo of the following composition was prepared and the dispersion stability of titanium dioxide was tested.

| Ammonium laurylsulfate | 15.0 wt. % |
|---|---|
| Lauric acid diethanolamide | 4.0 |

| | |
|---|---|
| Ethanol | 3.0 |
| Carboxy vinyl Polymer (Carbopole 941) | 0.5 |
| Triethanolamine | 2.0 |
| Titanium dioxide | 0.2 |
| Perfume | Suitable amount |
| Dye | Suitable amount |
| Water | Balance |

The thus-prepared shampoo had a viscosity of 350 cps (at 30° C.). After aging tests at 50° C., 40° C. and room temperature for three months, the titanium oxide was not precipitated and a stable dispersion was maintained.

EXAMPLE 2

| | |
|---|---|
| Triethanolamine laurylsulfate | 20.0 wt. % |
| Lauric acid diethanolamide | 3.0 |
| Propylene glycol | 10.0 |
| Carboxy vinyl Polymer (Carbopole 941) | 0.5 |
| Triethanolamine | 2.0 |
| Bismuth oxychloride* | 1.0 |
| Dye | Suitable amount |
| Perfume | Suitable amount |
| Water | Balance |

*Pigment with pearly gloss

The resulting shampoo had a viscosity of 450 cps (at 30° C.). After the same aging tests as described in Example 1, the bismuth oxychloride was not precipitated and a stable pearlescent appearance was maintained.

EXAMPLE 3

| | |
|---|---|
| Triethanolamine laurylsulfate | 18.0 wt. % |
| Lauric acid monoethanolamide | 2.0 |
| Carboxy vinyl Polymer (Carbopole 941) | 0.5 |
| Triethanolamine | 7.0 |
| Zinc pyrithione* | 1.0 |
| Perfume | Suitable amount |
| Dye | Suitable amount |
| Water | Balance |

*Water-insoluble germicide

The resulting shampoo had a viscosity of 500 cps (at 30° C.). After the same aging tests as described in Example 1, the zinc pyrithione was not precipitated and an excellent stability was exhibited.

The embodiments of the invention in which an exclusive property or privilege is claimed are defined as follows:

1. A liquid shampoo composition having an excellent foaming power and containing a water-insoluble powder dispersed therein in a stable condition, consisting essentially of:
    from 5 to 30 wt. % of ammonium salt, monoethanolamine salt, diethanolamine salt, triethanolamine salt or 2-amino-2-methylpropane-1,3-diol salt of anionic, synthetic, organic surfactant effective for shampooing hair;
    from 0.1 to 1.0 wt. % of water-soluble carboxy vinyl polymer;
    from 1 to 10 wt. % of a fatty acid alkanolamide having from 10 to 14 carbon atoms in the fatty acid moiety;
    from 1 to 20 wt. % of a stabilizer selected from the group consisting of alkyl monohydric alcohols having 1 to 3 carbon atoms, glycols having 2 to 6 carbon atoms, monoethanolamine, diethanolamine and triethanolamine;
    from 0.001 to 5 wt. % of water-insoluble, finely divided powder selected from the group consisting of water-insoluble pigments for shampoos, water-insoluble pearlescent agents for shampoos, water-insoluble hair or scalp-treating medicaments for shampoos and water-insoluble germicides for shampoos;
    said composition containing an amount of ammonia or an alkanolamine sufficient to maintain the composition at a pH of from 6 to 8;
    and the balance is essentially water.

2. A liquid shampoo as claimed in claim 1, containing from 10 to 20 wt. % of said anionic surfactant, from 0.4 to 0.6 wt. % of said carboxy vinyl polymer; from 3 to 5 wt. % of said fatty acid alkanolamide; and from 3 to 10 wt. % of said stabilizer.

3. A liquid shampoo according to claim 1 or claim 2 in which said anionic surfactant is an ammonium, monoethanolamine, diethanolamine, triethanolamine, or 2-amino-2-methylpropane-1,3-diol salt of alkyl sulfate having 8 to 22 carbon atoms in the alkyl group, polyoxyethylene (1 to 10 moles) alkyl ether sulfate having 8 to 22 carbon atoms in the alkyl group, polyoxyethylene (1 to 10 moles) alkylphenyl ether sulfate having 8 to 12 carbon atoms in the alkyl group, olefin sulfonate having 8 to 22 carbon atoms or alkylbenzene sulfonate having 9 to 18 carbon atoms in the alkyl group.

4. A liquid shampoo as claimed in claim 3 in which said stabilizer is selected from the group consisting of methyl alcohol, ethyl alcohol, isopropyl alcohol, ethylene glycol, diethylene glycol, propylene glycol, dipropylene glycol, hexylene glycol, monoethanolamine, diethanolamine and triethanolamine, and said water-insoluble powder is selected from the group consisting of calcium carbonate, barium carbonate, titanium dioxide, Hansa Yellow, crushed rock, talc, bismuth oxychloride, mica, fish scales and zinc pyrithione.

* * * * *